(12) United States Patent
Yu

(10) Patent No.: US 11,538,153 B2
(45) Date of Patent: Dec. 27, 2022

(54) NON-INVASIVE FUNCTIONAL ASSESSMENT TECHNIQUE FOR DETERMINING HEMODYNAMIC SEVERITY OF AN ARTERIAL STENOSIS

(71) Applicant: Huidan Yu, Indianapolis, IN (US)

(72) Inventor: Huidan Yu, Indianapolis, IN (US)

( * ) Notice: Subject to any disclaimer, the term of this patent is extended or adjusted under 35 U.S.C. 154(b) by 239 days.

(21) Appl. No.: 17/007,459

(22) Filed: Aug. 31, 2020

(65) Prior Publication Data

US 2022/0067922 A1 Mar. 3, 2022

(51) Int. Cl.
*G06T 7/00* (2017.01)
*A61B 5/02* (2006.01)
(Continued)

(52) U.S. Cl.
CPC .......... *G06T 7/0012* (2013.01); *A61B 5/0035* (2013.01); *A61B 5/02035* (2013.01); *A61B 5/7278* (2013.01); *A61B 5/7292* (2013.01); *A61B 8/06* (2013.01); *G06T 7/11* (2017.01); *G06T 2207/10081* (2013.01); *G06T 2207/10088* (2013.01); *G06T 2207/10132* (2013.01); *G06T 2207/30096* (2013.01); *G06T 2207/30104* (2013.01)

(58) Field of Classification Search
CPC ...................... G06T 7/0012; G06T 7/11; G06T 2207/10081; G06T 2207/10088;
(Continued)

(56) References Cited

U.S. PATENT DOCUMENTS

| | | | |
|---|---|---|---|
| 8,157,742 B2* | 4/2012 | Taylor ................ | A61B 5/02007 600/481 |
| 10,702,339 B2* | 7/2020 | Taylor .................. | G06V 20/698 |

(Continued)

OTHER PUBLICATIONS

Khan("Image based Computational Hemodynamics for Non-invasive and Patient-Specific Assessment of Arterial Stenosis") (Year: 2019).*

(Continued)

*Primary Examiner* — Emily C Terrell
*Assistant Examiner* — Molly Wilburn
(74) *Attorney, Agent, or Firm* — C. John Brannon; Brannon Sowers & Cracraft PC

(57) ABSTRACT

A computational methodology for noninvasively assessing the severity of arterial stenosis and predicting the therapeutic outcome of interventional treatment for stenosis assessed as severe, mild, or in between based on patient's CT/MRI imaging data, ultrasound test data, and physio-pathological material properties. The method includes two major parts. The steps in the first part comprise receiving medical data, segmenting the anatomical three-dimensional geometry of the stenosed artery, setting up boundary conditions at inlet and outlets using the ultrasound velocity waveforms together with 3-element WinKessel model, and computing pulsatile pressure waveforms proximal and distal to the existing stenosis for TPI. The steps in the second part comprise of varying the VR of the stenosis virtually from 0% to 95% with an increment of 5%, computing TPI for each level of VR, establishing the functional relation between TPI and VR, identifying the two thresholds of $VR_{mild}$ and $VR_{severe}$ on TPI-VR curve, determining the severity of the existing stenosis by comparing $VR_{existing}$ with $VR_{mild}$ and $VR_{severe}$ concurrently and predicting the outcome of the lesion (TPI) improvement after an interventional treatment such as stenting for the existing stenosis.

8 Claims, 4 Drawing Sheets

(51) Int. Cl.
  *A61B 8/06* (2006.01)
  *A61B 5/00* (2006.01)
  *G06T 7/11* (2017.01)

(58) Field of Classification Search
  CPC . G06T 2207/10132; G06T 2207/30096; G06T 2207/30104; A61B 5/0035; A61B 5/02035; A61B 5/7278; A61B 5/7292; A61B 8/06; A61B 6/504; A61B 8/0891; A61B 8/5223; A61B 6/5205; G16H 50/50
  See application file for complete search history.

(56) References Cited

U.S. PATENT DOCUMENTS

| | | | | |
|---|---|---|---|---|
| 2008/0287812 A1* | 11/2008 | Parlikar | | A61B 5/029 600/526 |
| 2013/0132054 A1* | 5/2013 | Sharma | | G16H 30/40 703/9 |
| 2013/0197884 A1* | 8/2013 | Mansi | | A61B 8/469 703/2 |
| 2014/0243663 A1* | 8/2014 | Taylor | | A61B 5/4848 600/504 |
| 2016/0228190 A1* | 8/2016 | Georgescu | | A61B 5/026 |

OTHER PUBLICATIONS

Yu ("Mass-conserved volumetric lattice Boltzmann method for complex flows with willfully moving boundaries") Phsysical Review (Year: 2014).*

An ("Unified mesoscopic modeling and GPU-accelerated computational method for image-based pore-scale porous media flows" International Journal of Heat and Mass Transfer (Year: 2017).*

Xu (Assessment of boundary conditions for CFD simulation in human carotid artery) Biomechanics and modeling in Mechanobiology. (Year: 2018).*

* cited by examiner

Translesional pressure indicator (TPI)
(TSPG=$P_a$-$P_d$ or FFR=$P_d$/$P_a$)

NON-INVASIVE FUNCTIONAL ASSESSMENT TECHNIQUE FOR DETERMINING HEMODYNAMIC SEVERITY OF AN ARTERIAL STENOSIS

TECHNICAL FIELD

The present invention relates generally to the field of precision medicine, and more particularly to the personalized diagnostics and therapeutics for arterial stenosis.

BACKGROUND OF THE INVENTION

Vascular disease, including coronary, extra-cranial, and peripheral arterial beds, significantly contributes to heart attacks, strokes, and lower extremity ischemia. Arterial stenosis is one of the most common vascular diseases and can lead to life- and limb-threatening consequences, including myocardial ischemia, ischemic stroke, and limb amputation.

Stenosis is a condition that involves blockage of blood flow due to an abnormal narrowing of an arterial lumen. Such a disease can be present in any artery. Coronary stenosis is a leading cause of morbidity and mortality worldwide. In the U.S., it was responsible for about 850 thousand deaths in 2016 with an annual total medical cost estimated at $351 billion. Carotid stenosis is another leading cause of large-vessel ischemic strokes. Each year about 800 thousand Americans have a new or recurrent stroke, resulting in health care costs of $34 billion. Peripheral stenosis affects 8 to 12 million Americans. The annual incidence of amputations in the U.S. is 185 thousand with a total of 2 million Americans living with limb loss. The annual direct therapeutic costs of amputation care are $13.7 billion. Given the great prevalence and significant consequences of arterial stenosis, non-invasive assessment for personalized treatment is vital to promote public health and reduce the medical cost.

Although stenosis can be observed by noninvasive imaging modalities, such as CT angiogram (CTA), magnetic resonance imaging (MRI), Doppler ultrasound sonography (DUS), and echocardiogram (ECHO), appropriate means in evaluating the true hemodynamic severity of stenosis are currently lacking in clinical practice. A gold standard is only available for coronary stenosis, for which the fractional flow reserve (FFR), defined as the ratio of the distal pressure $P_d$ to the proximal pressure $P_a$ of the stenosis (FFR=$P_d/P_a$), is used to determine the severity of myocardial ischemia caused by coronary stenosis. The clinical guideline is as follows: FFR<0.75 indicates significant coronary stenosis; FFR>0.8 suggests insignificant coronary stenosis; and if 0.75<FFR<0.8, the severity assessment requires additional pathophysiological information. While FFR is a reliable index, its clinical application is rather limited due to (a) the cumbersome nature of invasive pressure measurement via catheterization, (b) the risk of medical and surgical complications, and (c) the high cost of guidewires and measurement. Meanwhile, the applicability of FFR for stenoses in non-coronary arteries is questionable due to the differences in vasodilatory reserve (the maximum increase in blood flow through the artery above the normal resting volume) of different vascular beds. For example, the vascular reserve in the coronary circulation is 4-5 times baseline, whereas it may go up to 80 times in some peripheral circulation beds. It remains controversial as to how to define the hemodynamic severity of stenosis in non-coronary vascular beds. A popular way of assessing stenosis severity in non-coronary vascular beds is to use the trans-stenotic pressure gradient (TSPG). As opposed to the pressure ratio $P_d/P_a$ in FFR, TSPG is defined by the deviation of the distal pressure $P_d$ from the proximal pressure $P_a$, i.e. TSPG=$P_a-P_d$. Specifically, in an aorta-renal arterial segment, TSPG is the pressure drop between the aorta (proximal) and renal (distal) artery across renal stenosis. Evidence has shown that the severity of renal stenosis is closely associated with TSPG and that a decrease in renal pressure is a trigger of renovascular hypertension. Thus, TSPG has been used as an indicator to determine the level of blood flow blockage of renal stenosis. There is a consensus that renal stenosis is hemodynamically significant if its peak systolic TSPG is larger than 20 mmHg, although it has not been clinically proven. Previous studies also indicate that the volume reduction of the artery lumen is more closely tied to TSPG than diameter reduction that is heavily used in current clinical practice. Meanwhile, it is found that a functional relationship between TSPG and lumen volume reduction (VR) can be used to assess the true hemodynamic significance of renal stenosis.

The general understanding to date is that FFR is applicable for stenoses in coronary arteries and TSPG would be a popular alternative in assessing the severity of non-coronary stenosis. Either FFR or TSPG is calculated from the proximal and distal pressures to the stenosis, i.e. $P_a$ and $P_d$, respectively. The pressure field can be quantified by computational modeling and simulation. The undressed question is how to know if the non-coronary arterial stenosis is severe or mild after knowing the FFR and/or TSPG of it. The answer to this question is significantly important to avoid overusage or underusage interventional therapy, such as stenting, for stenosis.

SUMMARY OF THE INVENTION

In accordance with an aspect of the present invention, there is an established functional relationship between trans-lesional pressure indicator (TPI) and volume reduction (VR) of the arterial lumen through a virtual worsening of the stenosis. The TPI is referred to as either FFR for coronary stenosis or TSPG for non-coronary stenosis. The quantification of TPI on each virtual VR level is done by the unified and computational method and system (U.S. patent Ser. No. 10/482,215), resulting in a functional relationship between TPI and VR. The TPI-VR relation is used to determine the hemodynamic severity of arterial stenosis and predict the lesion improvement from an interventional treatment for stenosis.

On the TPI-VR curve, one can obtain two thresholds of VR, $VR_{mild}$ and $VR_{severe}$, corresponding to flat and steep slopes respectively. The hemodynamic severity of existing stenosis with a lumen volume reduction, $VR_{existing}$, can be determined by a personalized hemodynamic index that includes the two thresholds of VR for mild ($VR_{mild}$) and severe ($VR_{severe}$) stenosis as follows:

$VR_{existing} < VR_{mild}$: mild stenosis $VR_{mild} < VR_{existing} < VR_{severe}$: moderate stenosis $VR_{existing} > VR_{severe}$: severe stenosis The outcomes of lesion improvement from a potential interventional treatment for severe stenosis can be predicted based on the TPI corresponding to VR=0.

BRIEF DESCRIPTION OF THE DRAWINGS

For the purpose of illustration, there are shown in the drawings certain embodiments of the present invention. In the drawings, like numerals indicate like elements throughout. It should be understood that the invention is not limited to the precise arrangements, dimensions, and instruments shown. In the drawings.

DETAILED DESCRIPTION OF THE INVENTION

Figure 1:
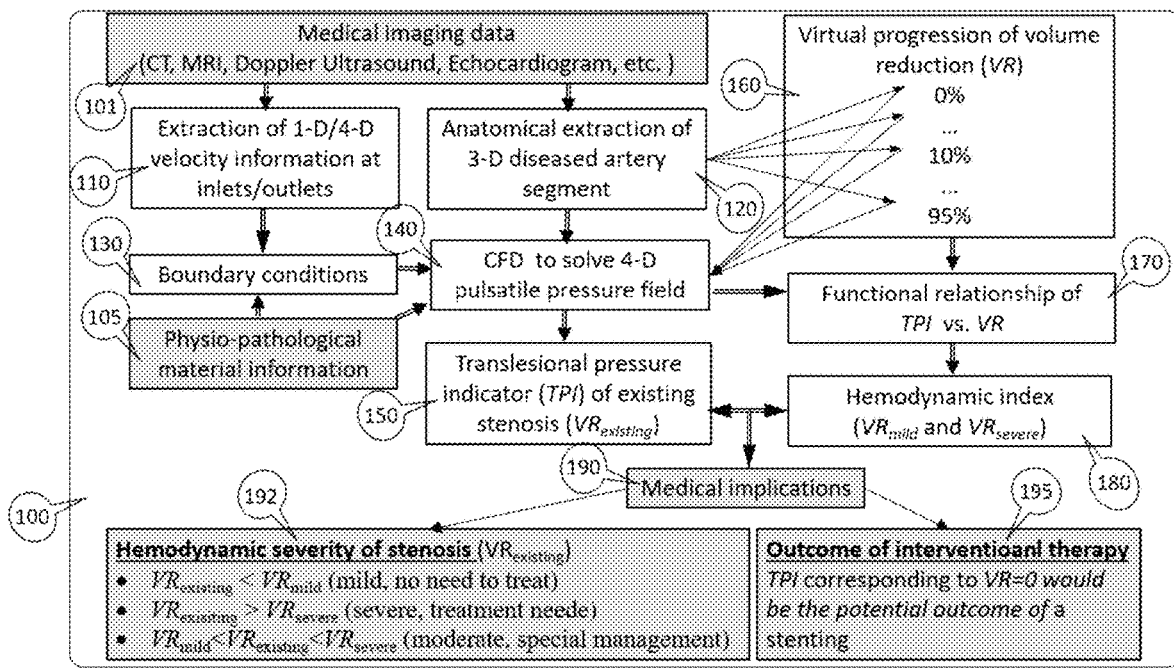
FIG. 1 illustrates a flowchart of a computation infrastructure from medical imaging data and physio-pathological material information of a patient to personalized medical implications for assessing the true hemodynamic severity of arterial stenosis and predicting the possible lesion improvement from an interventional treatment if the stenosis is determined severe.

Reference to the drawings illustrating various views of exemplary embodiments of the present disclosure is now made. In the drawings and the description of the drawings herein, certain terminology is used for conscience only and is not to be taken as limiting the embodiments of the present disclosure. Furthermore, in the drawings and the description below, like numerals indicate like elements throughout.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

In accordance with an exemplary embodiment of the present disclosure, there is provided a computational method that determines the hemodynamic severity of arterial stenosis (either mild, moderate, or severe) and predicts the potential outcome of lesion improvement from an interventional treatment, such as stenting, for severe stenosis. The method is non-invasive and personalized solely using the patient's noninvasive medical data from standard of care in the clinic. Computation software and/or open sources may be used to perform image segmentation to extract the flow domain and quantify VR and CFD to compute TPI across the stenosis. The detailed steps are described below. A functional relationship between TPI and VR is established through a virtual progression of the stenosis characterized by VR, from which the medical implications can be derived including the severity of the existing stenosis and the TPI improvement from an interventional treatment for the stenosis.

Figure 2:
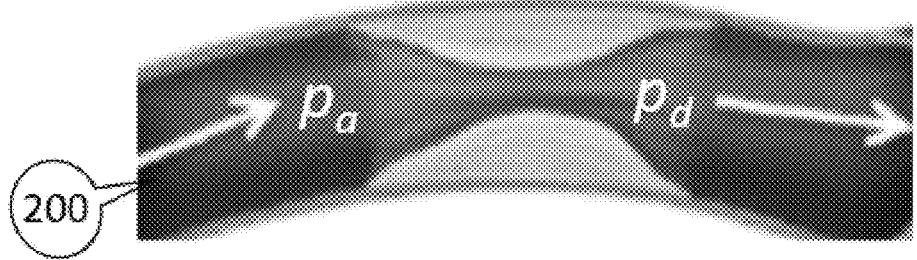
FIG. 2 illustrates the calculation of TPI from computed proximal pressure ($P_a$) and distal pressure ($P_d$) to the stenosis. TPI can be either FFR or TSPG based on the type of the stenosed artery.
Figure 3:
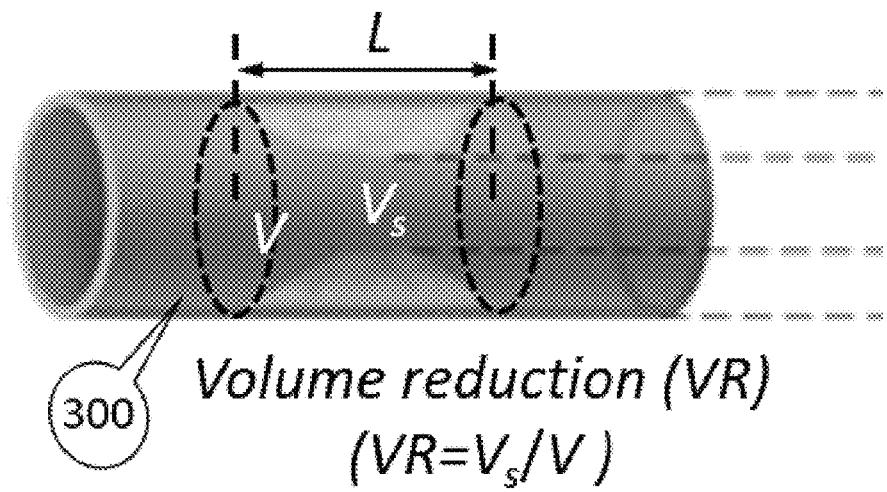
FIG. 3 illustrates the calculation of volume reduction (VR), defined as the ratio of lumen volume with stenosis ($V_s$) to the lumen volume without stenosis (V).

Referring now to FIG. 1, there is illustrated a flowchart of medical system architecture, generally designated as 100, for noninvasively quantifying the medical implications 190 of existing arterial stenosis based on patient's non-invasive medical imaging data 101 and physio-pathological material information 105. Computational modeling comprises image processing 110 and 120, CFD 140, virtual VR progression 160, and a functional relationship of TPI and VR 170. Through a repeated execution of CFD 140 with progressive VR 160 to quantify the corresponding TPI, a personalized functional relationship 170 TPI vs. VR is established. The important medical implications 190 that is to guide patient management and clinical treatment for stenosis can be derived. The TPI indicates the translesional pressure calculated from the proximal pressure ($P_a$) and the distal pressure ($P_d$) to stenosis whereas VR is the reduction percentage of the arterial lumen, as shown in FIGS. 2 and 3 respectively.

Figure 4:
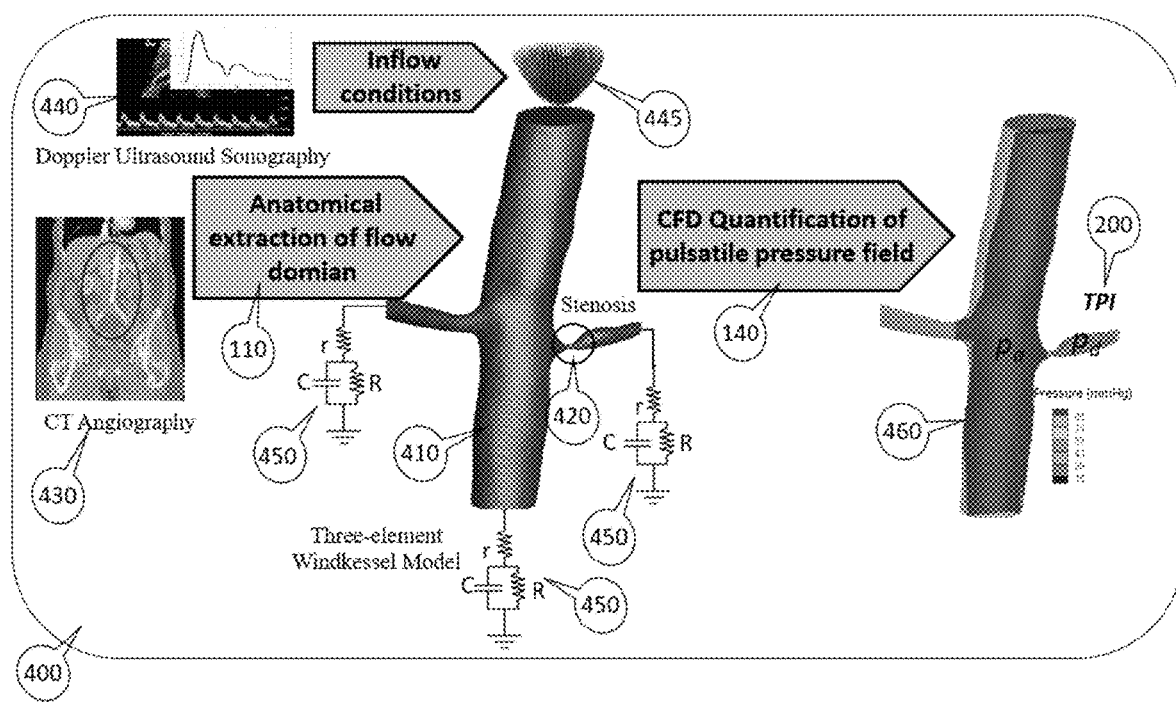
FIG. 4 is an exemplary embodiment of an aortorenal arterial system to illustrate the process of image-based computational fluid dynamics (CFD) from patient's medical imaging data and physio-pathological material information to TPI of existing renal stenosis via noninvasive computational modeling.

Referring now to FIG. 4, there is illustrated a computational method, generally designated as 400, to implement image processing 110, 120, and CFD 140 to get the TPI 150 for existing stenosis 420 through an exemplary embodiment of aortorenal artery system 410 with an existing stenosis 420, in this specific example a renal stenosis. A typical image-based CFD consists of three steps: (1) 3-D anatomical extraction 120 for the morphology of the stenosed aortorenal artery from CT image data 430, (2) quantification of 4-D hemodynamics 140 in the segmented artery system 430 using commercial or open-source CFD software by introducing patient's physio-pathological material information 105 and boundary conditions at inlet and outlets 130, and (3) calculation of TPI 200 from the computed pressure field 460. Physio-pathological material information 105 includes blood density, viscosity, and so on. One example of specific steps for image-based computational hemodynamics is described as follows. After medical imaging data, i.e. CTA, are received, image segmentation is performed first to extract the morphological flow domain including the stenosed artery. This computation domain, together with the flow information extracted from DUS images and the physiological quantities from the same patient will be introduced as the input of the CFD. Through CFD that may involve modeling of flow-structure interaction, non-Newtonian effect, and/or turbulence then quantify the pulsatile velocity vector and pressure fields for hemodynamics including TPI.

In general, the steps for image-based computational hemodynamics are after medical imaging data, such as CTA, are received, image segmentation is performed first to extract the morphological flow domain including the stenosed artery. This computation domain, together with the flow information extracted from DUS images and the physiological quantities from the same patient are introduced as an input of the CFD.

Through CFD that may involve modeling of flow-structure interaction, non-Newtonian effect, and/or turbulence, the pulsatile velocity vector and pressure fields for hemodynamics including TPI are then quantified.

For example, one method for noninvasively quantifying a translesional pressure indicator of existing arterial stenosis may include the steps of first receiving a patient's medical data including CT/MRI imaging data, ultrasound velocity wave information, and physio-pathological material information such as blood viscosity and density and then extracting velocity waveforms from ultrasound sensor positioned at extracted blood flow domain inlet and outlets. Next, the translesional pressure indicator of arterial stenosis is quantified such as by using a unified computational method and a three-element Windkessel model. Anatomical information is then extracted from the CT/MRI imaging data, and the translesional pressure indicator is computed for the existing arterial stenosis.

In another example, a noninvasive method for determining the hemodynamic severity of arterial stenosis (mild, severe, or moderate) and predicting possible lesion improvement from an interventional treatment for existing stenosis may include first virtually increasing the severity of (i.e, worsening) the stenosis by varying lumen volumetric reduction (VR) levels from 0% to 95%, wherein stenosis shape remains substantially constant. The translesional pressure indicator (TPI) value for each lumen volumetric reduction level is computed with a three-element Windkessel model (WK3 model), wherein the flow domain excepting the existing stenosis and inlet boundary conditions remain the same subject to adjustment of r, C, and R parameters in the WK3 model. A functional relationship is then established between TPI and lumen volumetric reduction along a curve of TPI=TPI(VR), and two thresholds of mild volume reduction ($VR_{mild}$) and severe volume reduction ($VR_{severe}$) are identified based on analysis of the TPI=TPI(VR) curve. The severity of the existing stenosis is determined by comparing existing volume reduction ($VR_{existing}$) with $VR_{mild}$ and $VR_{severe}$, and a probable outcome of TPI after an interventional treatment is predicted.

Since only a segment of vessel anatomy is included in the CFD due to the current practical limit of computational power to conduct a computation for the entire artery network of the human body, boundary conditions are needed at inlets and outlets of the segmented arterial system to accurately represent the vascular network outside of the local domain. The patient's ultrasound test image 440 provides a velocity waveform 445, as the inlet flow condition, either a parabolic flow profile using the Poiseuille solution for flow in a circular pipe or an analytical solution for Womersley flow in a pipe based on the velocity waveform. The choice of outflow conditions is diverse including zero pressure or zero traction conditions, resistance or impedance conditions, reduced-order models which can be open or closed loop, or reduced-order one-dimensional wave propagation equations. To capture the interaction between the local three-dimensional domain and the global circulation, the three-dimensional CFD solver must be coupled to a reduced-order lumped parameter network model. The 3-element WindKessel model (WK3) has been commonly used to construct such a network, in which a Windkessel circuit 450 is adapted to model the distal vasculature with one capacitor, modeling vessel compliance, and two resistors, modeling proximal and distal pressure drops respectively. As a result, WK3 is also known as the RCR model. Evidence has shown that WK3 can well reproduce physiological pressure waves in large vessels.

Figure 5:
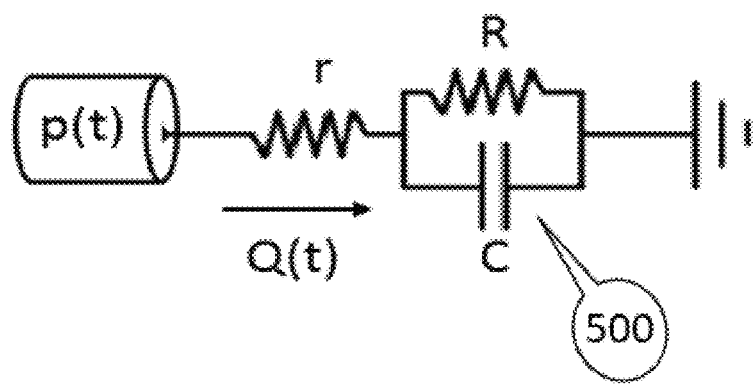
FIG. 5 illustrates the three-element WindKessel (WK3) model for outlet boundary conditions consists of one capacitor (C) modeling vessel compliance and two resistors (r and R) modeling proximal and distal resistance, respectively. The WK3 model is used to determine the dynamic pressure P(t) at the artery outlet affected by the flow rate Q(t) and the three parameters.

Illustrated in FIG. 5, WK3 is an analogy to an electrical circuit, which models the distal vasculature with one capacitor, C, modeling vessel compliance, and two resistors, r and R, modeling proximal and distal resistance respectively, thus also known as RCR model. The flow (Q) and the mean pressure (P) over these boundaries are related by an ODE $$\frac{dp}{dt} + \frac{1}{RC}p = r\frac{dQ}{dt} + \frac{1}{RC}(r+R)Q. \tag{1}$$

where r and R represent the proximal and distal resistances, and C is the compliance of the distal vasculature. Specifically, r is used to absorb the incoming waves and reduce artificial wave reflections. It has been well-known that WK3 is an appropriate outlet BC model among other physiologically relevant 0-D outflow models to simulate the peripheral vasculature and should be used when significant compliance is located in the modeled distal vasculature. Equation (1) has an analytical solution $$p(t) = e^{-t/(RC)} \int_0^t e^{0/(RC)} \left[ rdQ(s)/ds + \left(r + \frac{RQ(s)}{RC}\right) \right] ds + p_0 \tag{2}$$

where $p_0$ is the initial pressure at the outlet. It should be noted that the RCR circuit can be used as a BC for large vessels such as the aorta and branch vessels going to the head and neck. In patient-specific computational hemodynamics, the three elements, r, C, R, specified at each outlet, must be tuned to obtain the physiological values for the mean total flow rate ($Q_{out}$) at the outlets and target systolic ($p_{sys}$) and diastolic ($p_{dia}$) pressure, with the mean arterial pressure, $p_{in}=(p_{sys}+2p_{dia})/3$, at the inlet based on patient's clinical data. For an aortorenal system, brachial pressure for a base of pressure and MRI or DUS imaging data based on the availability of the flow target value ($Q_{out}$) were used With the understanding that the capacitor and resistor have independent functionalities in the WK3 circuit: a capacitor reflects the pulsatility of blood flow whereas a resistor determines the flow rate.

Figure 6:
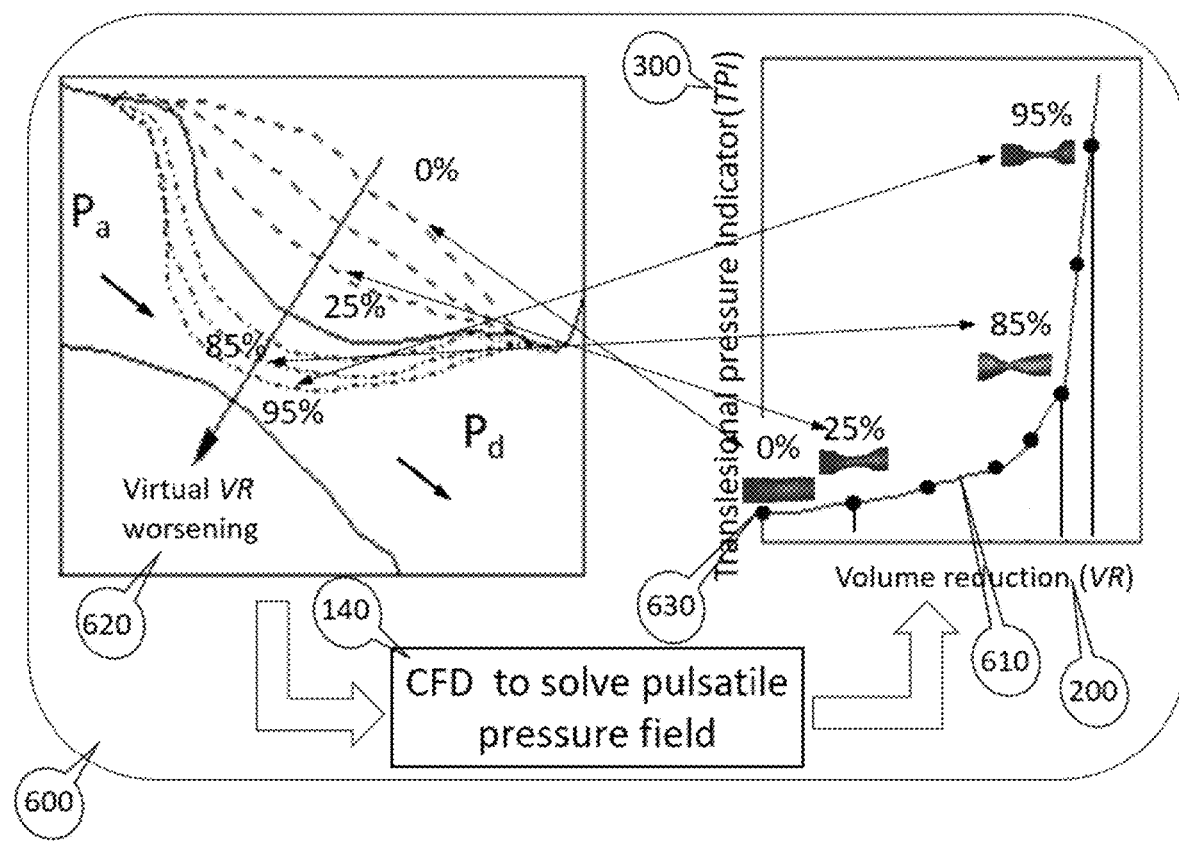
FIG. 6 illustrates the establishment of a TPI-VR functional relationship through a virtual progression of the stenosis characterized by the VR of the arterial lumen. CFD is repeatedly executed to quantify TPI for each level of VR.

Referring now to FIG. 6, there is illustrated a computational method, generally designated as 600, to establish a personalized functional relation 610 between TPI 300 and VR 200 via a virtual VR worsening progression 620. CFD 140 is repeatedly executed at each VR level 620 to quantify the corresponding TPI. Although the TPI can be computed by CFD 400, it cannot directly determine the hemodynamic severity of the stenosis in general. The instant method is to virtually deteriorate the stenosis by increasing the VR from 0% to 95% with an increment of 5% 620. Through the repeated CFD quantification of TPI 400 for each level of VR, a functional relationship between TPI and VR 610 can be established. When VR is worsened, the shape of the three-dimensional stenosis remains similar to the maximum extent. It is noted that VR=0% corresponds to the removal of stenosis.

Figure 7:
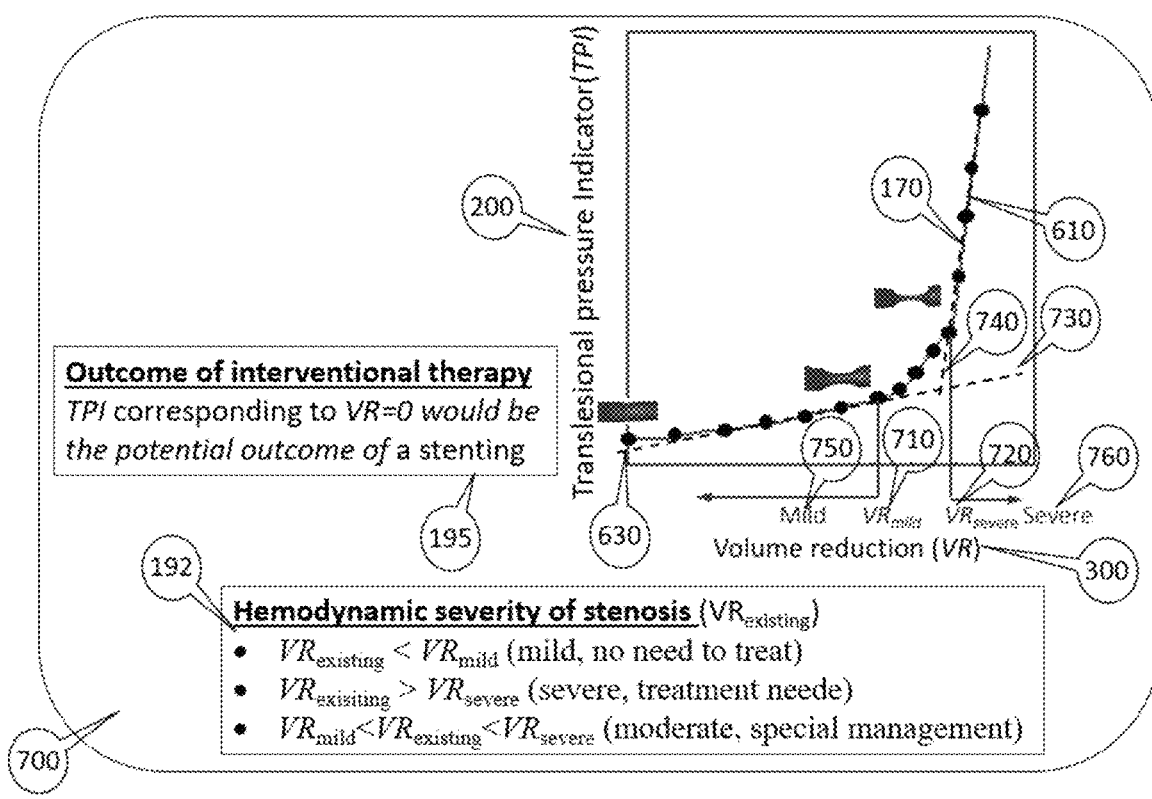
FIG. 7 illustrates the determination of hemodynamic index including two thresholds of VR, i.e. $VR_{mild}$ and $VR_{severe}$, based on the piece-wise slopes on the TPI-VR curve and the values of TPI. Comparing the $VR_{existing}$ of the existing stenosis with the hemodynamic index (two VR thresholds), the hemodynamic severity of the stenosis can be determined. Meanwhile, the potential outcome of lesion improvement from interventional therapy, such as stenting, can be recognized by the TPI at VR=0.

Referring now to FIG. 7, there is illustrated a computational method, generally designated as 700, to derive the medical implications 192 and 195 in FIG. 1 from the TPI-VR relationship 610 in FIG. 6. Two thresholds of VR, i.e. $VR_{mild}$ 710 and $VR_{serve}$ 720, can be identified through the piece-wise slopes 730 and 740, respectively. These two thresholds form the hemodynamic index for medical use. The criteria of mild 750 and severe 760 stenoses are $VR<VR_{mild}$ and $VR>VR_{serve}$ respectively. Comparing the VR of the existing stenosis 420, characterized by $VR_{existing}$, with the hemodynamic index, the severity of the stenosis, either mild, severe, or moderate, can be determined, together with the suggestion of medical treatment 192. If the stenosis is determined as severe, the TPI at VR=0 630 indicates the outcome of the TPI improvement from a potential interventional treatment such as stenting 195.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

What is claimed is:

1. A method for noninvasively quantifying a translesional pressure indicator of existing arterial stenosis:
   a) receiving a patient's medical data including CT/MRI imaging data, ultrasound velocity wave information, and physio-pathological material information such as blood viscosity and density;
   b) extracting velocity waveforms from the ultrasound sensor positioned at extracted blood flow domain inlet and outlets;
   c) quantifying translesional pressure indicator of arterial stenosis using a unified computational method and a three-element Windkessel model;
   d) extracting anatomical information from the CT/MRI imaging data; and
   e) computing the translesional pressure indicator for the existing arterial stenosis.

2. The method of claim 1, wherein step b) further comprises:
   b1) segmenting three-dimensional blood flow domain including arterial stenosis with locations of inlet and outlets based on ultrasound; and
   b2) quantifying volume reduction ($VR_{existing}$) for existing stenosis.

3. The method of claim 1, wherein step c) further comprises:
   c1) constructing an adaptive parabolic velocity field to drive the flow in the flow domain using the velocity waveform at the inlet;
   c2) tuning R, C, and r parameters in the three-element Windkessel model for boundary conditions at outlets using the extracted velocity waveforms.

4. The method of claim 1, wherein step d) further comprises:
   d1) computing a pulsatile pressure field in a segmented artery;
   d2) calculating mean arterial pressure proximal and distal to the stenosis; and
   d3) calculating a translesional pressure indicator.

5. A noninvasive method for determining the hemodynamic severity of arterial stenosis (mild, severe, or moderate) and predicting possible lesion improvement from an interventional treatment for existing stenosis:
   a) virtually worsening the stenosis by varying lumen volumetric reduction (VR) levels from 0% to 95%, wherein stenosis shape remains substantially constant;
   b) computing a translesional pressure indicator (TPI) value for each lumen volumetric reduction level with a three-element Windkessel model (WK3 model); wherein the flow domain excepting the existing stenosis and inlet boundary conditions remain the same subject to adjustment of r, C, and R parameters in the WK3 model;
   c) establishing a functional relationship between TPI and lumen volumetric reduction along a curve of TPI=TPI (VR);
   d) identifying two thresholds of mild volume reduction ($VR_{mild}$) and severe volume reduction ($VR_{severe}$) based on analysis of the TPI=TPI(VR) curve;
   e) determining the severity of the existing stenosis by comparing existing volume reduction ($VR_{existing}$) with $VR_{mild}$ and $VR_{severe}$;
   f) predicting an outcome of TPI after interventional treatment.

6. The method of claim 5, wherein step d) comprises:
   a) if $VR_{existing} < VR_{mild}$, the stenosis is mild and thus there is no need to treat;
   b) if $VR_{existing} > VR_{severe}$, the stenosis is severe requiring immediate interventional treatment;
   c) If $VR_{mild} < VR_{existing} < VR_{severe}$, the stenosis is moderate, special handling is needed for the best patient management.

7. The method of claim 5 wherein the interventional treatment is placing a stent.

8. A method for noninvasively quantifying a translesional pressure indicator of existing arterial stenosis and predicting possible lesion improvement from an interventional treatment for existing stenosis, comprising:
   a) receiving a patient's CT/MRI imaging data, ultrasound velocity wave information, blood viscosity, and blood density;
   b) extracting velocity waveforms from ultrasound sensors positioned at an existing arterial stenosis blood flow inlet and outlet;
   c) quantifying a translesional pressure indicator of arterial stenosis between the blood flow inlet and outlet;
   d) extracting anatomical information from the CT/MRI imaging data; and
   e) computing the translesional pressure indicator for the existing arterial stenosis over a virtual lumen volumetric reduction range from 0% to 95%;
   f) building a functional relationship curve of TPI=TPI (VR);
   g) identifying two thresholds of $VR_{mild}$ and $VR_{severe}$ based on analysis of the TPI=TPI(VR) curve;
   h) determining the severity of the existing stenosis by plotting $VR_{existing}$ with $VR_{mild}$ and $VR_{severe}$; and
   i) predicting an outcome of TPI after interventional treatment.

* * * * *